United States Patent [19]

Marder

[11] Patent Number: 4,863,451
[45] Date of Patent: Sep. 5, 1989

[54] APPARATUS FOR DISPENSING INJECTABLE MEDICATION

[76] Inventor: Herbert B. Marder, 177 Lakewood Pl., Highland Park, Ill. 60035

[21] Appl. No.: 130,520

[22] Filed: Dec. 9, 1987

[51] Int. Cl.$^4$ .............................................. A61B 19/00
[52] U.S. Cl. ..................................... 604/403; 206/366
[58] Field of Search ............................. 604/403, 404; 206/363–366

[56] References Cited

U.S. PATENT DOCUMENTS

| | | | |
|---|---|---|---|
| 2,790,547 | 4/1957 | Sutton | 206/363 |
| 3,032,186 | 5/1962 | Jenkins | 206/365 |
| 3,058,584 | 10/1962 | Marshall | 206/365 |
| 3,351,210 | 11/1967 | Murcott | 206/364 |
| 4,085,845 | 4/1978 | Perfect | 206/363 |
| 4,349,338 | 9/1982 | Heppler | 206/364 |
| 4,658,957 | 4/1987 | Guth et al. | 206/365 |
| 4,767,008 | 8/1988 | Warnecke et al. | 206/366 |

*Primary Examiner*—Max Hindenburg
*Attorney, Agent, or Firm*—Robert M. Wolters

[57] ABSTRACT

A tray is provided for dispensing injectable medication which comprises a transverse ridge having a plurality of parallel valleys therein, each receiving a syringe. An opening is disposed adjacent each valley for receipt of bottles of medication, and a slot is disposed adjacent each valley for receipt of a patient card with patient information thereon. A well is provided in the tray, and as each cap is removed from a respective syringe it is placed in the well with the open end of the cap facing upwardly. After use of the respective syringe the needle is inserted into the cap in the well without the necessity of manual engagement of the cap, thereby avoiding the possibility of needle stick.

3 Claims, 2 Drawing Sheets

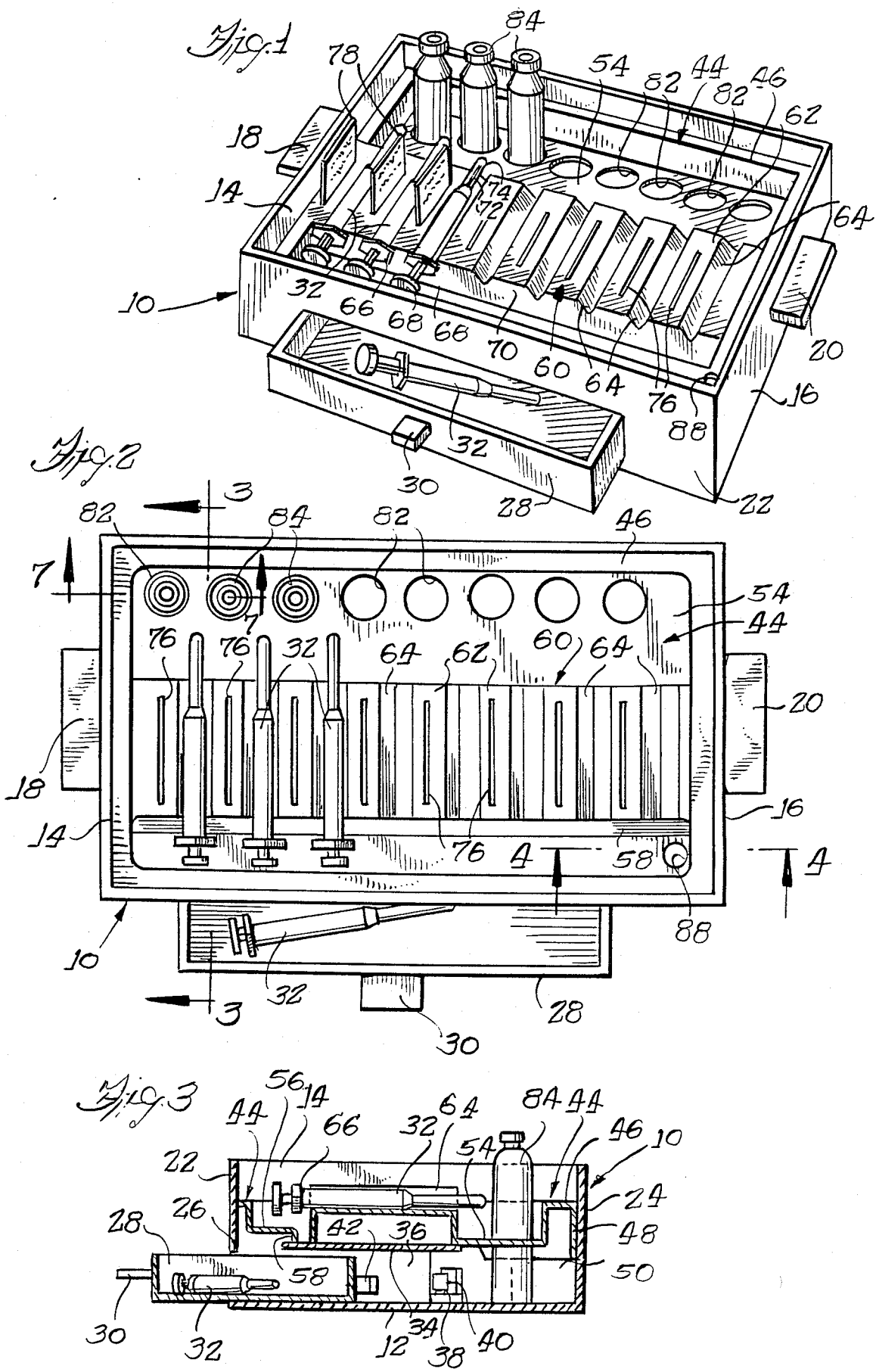

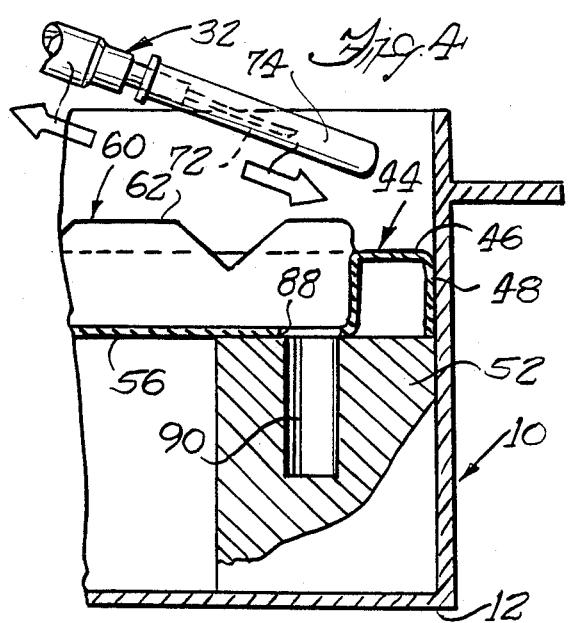
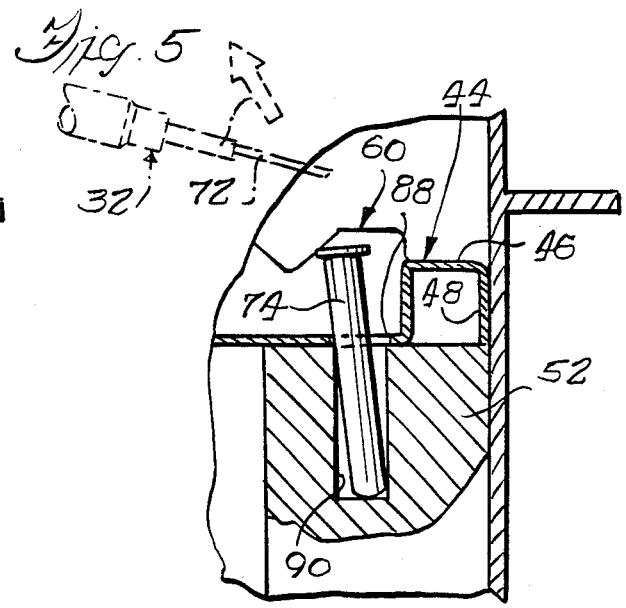
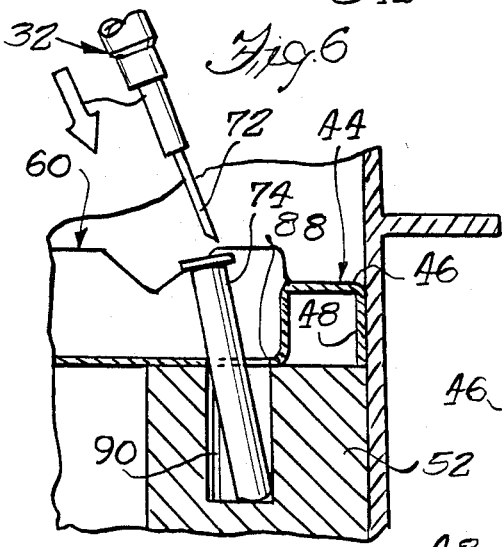
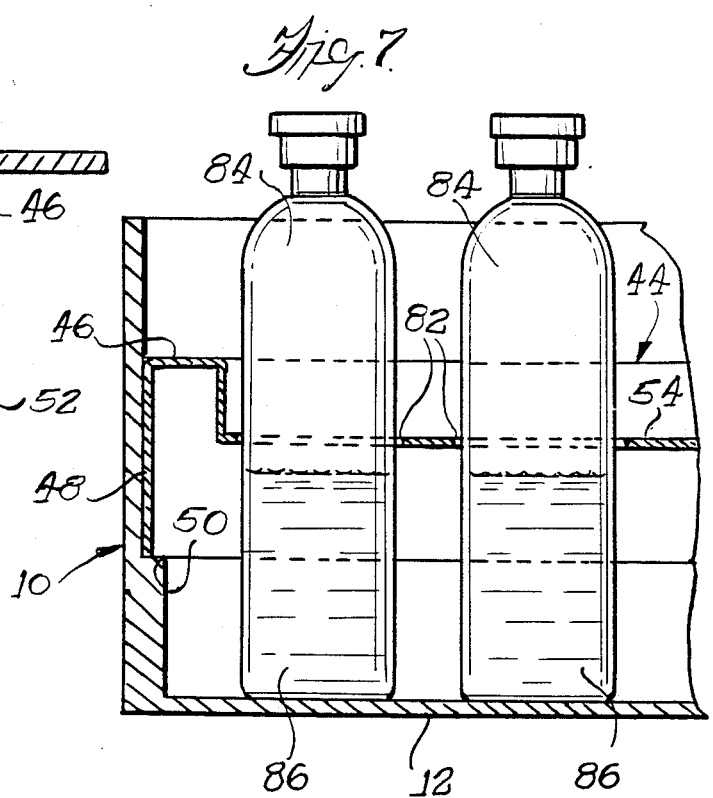
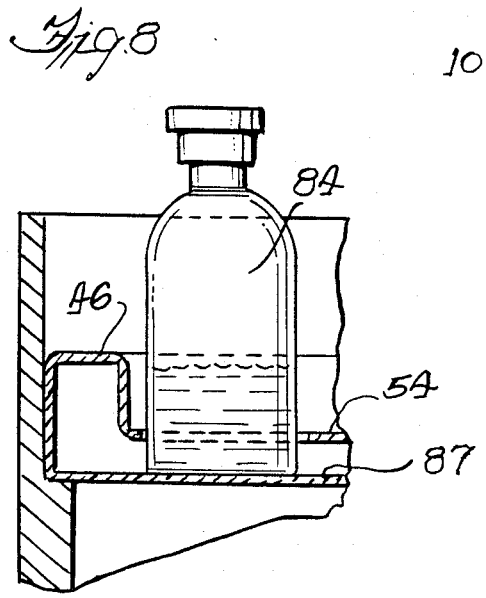

4,863,451

APPARATUS FOR DISPENSING INJECTABLE MEDICATION

BACKGROUND OF THE INVENTION

In hospitals and in nursing homes it is common practice to inject medication into a plurality of patients at approximately the same time. It is time-consuming and inefficient for a physician or nurse to have to load an individual syringe with medication essentially at the time that the injection is to be given to the patient, particularly when there are many patients. Furthermore, once a syringe has been used for injection, and even more so when used for withdrawal of a blood specimen, the syringe must be regarded as contaminated. It is known that AIDS, hepatitis, and other transmittable diseases can be transferred by contaminated syringes. Every health care professional who handles syringes or hypodermic needles has at sometime or another accidentally stuck himself in a finger with a contaminated syringe or hypodermic needle. This is now a potentially fatal accident following the advent of AIDS. In addition to the death or illness that can come to a health care professional who has stuck himself with a contaminated needle, there is a great potential financial liability on the part of the employer of the health care professional.

OBJECTS AND SUMMARY OF THE PRESENT INVENTION

It is an object of the present invention to provide a syringe tray in which pre-filled syringes are stored with caps covering needles prior to use, the tray being provided with an individual identification card for each syringe, and further having provision for supporting a bottle of medication in close proximity to each syringe.

It is a further object of the present invention to provide a syringe tray as just described which has provision for supporting the cap of a syringe which is in use in such a position that the caregiver can reinsert the needle in the cap without touching the cap, thus allowing positioning of the hand that is not holding the syringe in a position where it cannot possibly be engaged by the contaminated needle.

In carrying out the foregoing and other objects and advantages of the present invention, I have provided a syringe tray with a generally central raised rib having transverse valleys therein, each adapted to receive and store a syringe with a cap on the needle. Means is provided for respectively storing bottles of medication substantially directly opposite each syringe, which medication corresponds to the medication taken up by the syringe, thereby avoiding problems of confusion as to what medication is in which syringe. In addition, slots are provided between the valleys for receipt of medication cards indicating the name of the patient, the medication he is to receive, and the dosage thereof. The tray further is provided with a well in which each syringe cap is sequentially placed as a respective syringe is used. The cap is held in upright position, and when the use of a given syringe has been completed, it is only necessary for the caregiver to insert the needle back into the cap, without the necessity of handling the cap, and thereby exposing fingers for possible accidental needle sticks.

THE DRAWINGS

The present invention will best be understood from the following specification when taken in connection with the accompanying drawings wherein:

FIG. 1 is a perspective view of a syringe tray constructed in accordance with the principals of the present invention;

FIG. 2 is a top view on an enlarged scale of the syringe tray;

FIG. 3 is a cross sectional view taken substantially along the line 3—3 in FIG. 2;

FIG. 4 is a fragmentary vertical sectional view on an enlarged scale taken substantially along the line 4—4 in FIG. 2;

FIG. 5 is a view similar to FIG. 4, but showing the parts as positioned a few seconds after the position of FIG. 4;

FIG. 6 is a view similar to FIGS. 4 and 5, and showing the parts in position several seconds later after the injection has been completed and the needle is being returned to its storage position within the cap;

FIG. 7 is a fragmentary longitudinal sectional view taken substantially along the line 7—7 in FIG. 2; and FIG. 8 is a view similar to a portion of FIG. 7 showing a modification of the invention.

DETAILED DESCRIPTION OF THE DISCLOSED EMBODIMENTS

Turning now in greater particularity to the drawings, and first to FIGS. 1-3, there will be seen a tray 10 which is preferably constructed of a suitable plastic resin material. Portions of the tray preferably are molded by conventional techniques, the portions then being secured together by a suitable means such as sonic welding, adhesives, or solvents. The tray 10 includes a flat bottom 12 and integral end walls 14 and 16. The end walls include preferably integral outwardly extending handles 18 and 20 for gripping by the fingers to carry the tray. The tray further includes a front wall 22 and a back wall 24 integral with the bottom end wall, the four walls all being of the same height. The front wall 22 is provided in the bottom central portion thereof with an opening 26 through which a drawer 28 slides and rests on the bottom wall 12. A handle 30 extends forwardly from the drawer. The drawer and handle preferably comprise a one piece plastic molding. Used syringes or hypodermic needles may be placed in the drawer pending further disposal, and one such syringe is shown at 32. A horizontal wall 34 overlies the drawer 28 when the drawer is in closed position. This wall is supported on spacers 36 at either side of the drawer and parallel to the sides of the drawer. Stops 38 spaced inwardly somewhat from the walls 36 are engaged by the inner end of the drawer to limit insertion of the drawer to fully closed, but not over closed, position. A cabinet latch 40 preferably of the type having a pair of confronting rollers spring biased toward one another is mounted centrally of the tray from side to side, and substantially on a line with the stops 38. A projection 42 suitably secured to the rear wall of the drawer, and having an enlargement at the remote end, projects between the rollers of the latch 40 to hold the drawer in closed position.

A supporting shelf 44 is provided with a peripheral rim 46 having a depending flange 48 supported on shoulders 50 (FIGS. 3 and 7), and on a block 52 (FIGS. 4-6) in the front right corner of the tray and suitably secured to the bottom wall 12, the front wall 22, and the end wall 16 as by an adhesive.

Inwardly of the rim 46 the support 44 has a relatively deep (front to back) floor 54, this being a rear floor, and a relatively narrow front floor 56 which may be coplanar with the floor 54, or raised slightly relative thereto. A relatively narrow trough 58 extends downwardly from the rear edge of the front floor 56 and has the bottom thereof resting on and suitably secured, as by an adhesive, to the top of the wall 34, as is the rear wall 54.

Intermediate rear wall or floor 54 and the front wall or floor 56 there is a raised ridge 60 running from end to end of the support 44. The ridge 60 has an elevated top surface 62 spaced above the top surface of the rim 46 and interrupted by a plurality of V-shaped valleys 64 adapted to hold syringes 32 in horizontal position. The finger pieces 66 of the syringes and the plungers 68 thereof lie forwardly of the front edge 70 of the ridge, while the needles 72 protected by caps 74 lie partially within the valleys 64 and partially extending therefrom over the rear floor 54. The ridge 60 is designed to hold a plurality of syringes 32 in spaced, parallel relation, and in the illustrative example there are eight valleys 64 to receive up to eight syringes.

Immediately to the left of each valley 64 and parallel thereto there is provided an elongated slot 76 in the top wall 62 adapted to receive a patient card 78. Each patient card 78 indicates the name of the patient who is to get the shot in the syringe immediately to the right of the card, an identification of the medication and quantity thereof, and the name of the doctor who provided the perscription. Other information may be included if desired.

Toward the rear of the floor 54 adjacent the rim 46 and respectively aligned with the slots 76 there is a plurality of circular aperatures 82, which respectively receive medicine bottles 84 containing the medication noted on the patient cards respectively aligned therewith. The medicine bottles 84 are the standard 10 ml cylindrical bottles having a rubber seal at the top through which the syringe needle may be inserted for withdrawal of a desired dose of medication.

In accordance with one embodiment of the invention (FIG. 7) the bottles are too short to rest on the floor 12 of the tray, and cylindrical extenders 86, which may be of wood or other suitable materials, are secured to the bottoms of the bottles by means such as tape wrapped around the junction between each bottle and cylindrical support 86. Preferably each cylindrical support 86 is provided with a label having adhesive thereon indicating the name of the patient, the identification and dosage of medication, the time of day when it is to be given, and the name of the doctor and prescription number. In a second embodiment of the invention (FIG. 8) a sub-floor 87 is provided spaced slightly below the floor 54 so that the bottles may rest directly on the subfloor without the provision of the extenders 86.

In the front floor 56 adjacent the right end thereof, and somewhat beyond the last valley 64, there is provided a hole 88 somewhat to the right of the rightmost trough or valley 64. This hole is aligned with and opens into a well 90 in the block 52 (FIGS. 4-6). The significance of the hole 88 and well 90 will best be understood with reference to FIGS. 4-6.

A syringe 32 to be used in giving a shot or injection of medication is brought into proximity with the well 90 as shown in FIG. 4. The syringe cap 74 is manually removed and placed in the well as shown in FIG. 5, while the syringe is moved away from the tray to inject the medication into the patient. Following the injection the syringe is moved into substantial alignment with the cap 74 as shown in FIG. 6, and the needle is pushed down into the cap, whereby the cap is reassembled with the syringe without the necessity of placing any fingers on the cap 74, and thereby avoiding any possibility of the now-dreaded needle stick by the needle 72 which has been inserted into the body of a patient to inject the medication.

The complete structure of the invention has now been described. Most of the function will be understood from what has gone before. The tray is "loaded" in a location remote from the patients, such as a supply room or medicine room. The medication bottles 84 are in the holes 80 of the back floor 54, or are inserted therein if fresh ones are needed. The fresh syringes 32 are removed from their sterile wraps and placed in the troughs or valleys 64 next to the patient cards which previously have been inserted. When each of the syringes has been loaded from the respective bottle, the tray is carried to a location where the patients will congregate for shots, or the tray may be carried successively from one patient room to another for giving the shots or injections. In each case, once the syringe cap 74 has been removed and placed in the well, it is thereafter unnecessary to touch the cap. As has been explained previously, this avoids the possibility of needle stick which could be serious or fatal.

The specific embodiments of the invention as herein shown and described are for illustrative purposes only. Various changes in structure will no doubt occur to those skilled in the art, and will be understood as forming a part of the present invention insofar as they fall within the spirit and scope of the appended claims.

The invention is claimed as follows:

1. Apparatus for dispensing injectable medication comprising a tray having a raised ridge having a plurality of recesses for respective receipt of a plurality of syringes comprising valleys in said ridge transverse thereof and defining ridge portions between the successive valleys, said tray having means providing a like plurality of openings respectively positioned adjacent and spaced from said ridge axially of said valleys and substantially aligned with said ridge portions for respective receipt of a plurality of bottles of medication, each ridge portion including a slot substantially parallel to an adjacent valley and aligned with a respective valley for receipt of a patient card, and means for retaining the cap from a syringe during injection by that syringe, the open end of the cap being accessible for receipt of the needle end of the syringe without manual engagement of said cap.

2. Apparatus as set forth in claim 1 wherein there is only a single cap retaining means comprising an upwardly opening well for said plurality of syringe receiving recesses for temporarily receiving a succession of syringe caps.

3. Apparatus as set forth in claim 1 wherein said tray further includes a drawer for receipt of used syringes.

* * * * *